United States Patent [19]
Masuda

[11] Patent Number: 4,717,254
[45] Date of Patent: Jan. 5, 1988

[54] STRAY-LIGHT SUPPRESSOR FOR LITTROW SPECTROSCOPE

[75] Inventor: Toshizo Masuda, Tokyo, Japan
[73] Assignee: Ando Electric Co., Ltd., Tokyo, Japan
[21] Appl. No.: 894,610
[22] Filed: Aug. 7, 1986

[30] Foreign Application Priority Data

Aug. 26, 1985 [JP] Japan ............................ 60-129742[U]
Aug. 26, 1985 [JP] Japan ............................ 60-129743[U]

[51] Int. Cl.$^4$ .............................................. G01J 3/22
[52] U.S. Cl. ..................................................... 356/334
[58] Field of Search ........................ 356/305, 328, 334

[56] References Cited

U.S. PATENT DOCUMENTS 3,753,618  8/1973  Haley .................................... 356/334
4,300,835  11/1981  Schiemann et al. ................. 356/334

*Primary Examiner*—Vincent P. McGraw
*Attorney, Agent, or Firm*—Panitch Schwarze Jacobs and Nadel

[57] ABSTRACT

In a Littrow spectroscope including a concave mirror for reflecting light from a source, a diffraction grating for further reflecting the light reflected by the mirror, the grating being made rotatable to allow the mirror to re-reflect the light therefrom, and an exit on which the light re-reflected by the mirror is focused; a stray-light suppressor in the form of a strip is disposed in front of, and horizontally in parallel with the longitudinal central axis of, the mirror. The suppressor is held in front of the mirror at a distance of (L1-L2), where L1 is the distance between the mirror and the grating and L2 is the distance between the grating and the exit. The suppressor portion upon which the stray light from the diffraction grating impinges is tapered.

2 Claims, 7 Drawing Figures

STRAY-LIGHT SUPPRESSOR FOR LITTROW SPECTROSCOPE

BACKGROUND OF THE INVENTION

This invention relates to a stray-light suppressor for eliminating stray light, or the light of wavelengths other than of desired lengths which otherwise reaches the exit for outgoing light of a Littrow spectroscope.

Littrow spectroscope is an optical instrument for taking out an output of light of given wavelengths from the spectrum of a halogen lamp showing wide-band components.

The construction of an ordinary Littrow spectroscope is schematically shown in FIG. 1. Numeral 1 designates a light source, 2 a lens, 3 a slit, 4 a plane mirror, 5 a concave mirror, 6 a diffraction grating, 7 an exit, and 8 a beam of outgoing light.

Light from source 1 travels in the direction of the arrows in FIG. 1 toward exit 7. The full and broken lines indicate the width of optical path.

Light advances from source 1 in the following way:
(a) It is first reflected by plane mirror 4 toward concave mirror 5.
(b) Reflected light from concave mirror 5 reaches diffraction grating 6.
(c) Diffraction grating 6 reflects light back to concave mirror 5.
(d) Re-reflected light from concave mirror 5, while being focused, reaches exit 7.

Since diffraction of light takes place on the surface of diffraction grating 6, rotation of the grating causes light beams of varying wavelengths to appear, in succession, at exit 7.

Depending on the angle of diffraction grating 6 so rotated, reflected light may shuttle between concave mirror 5 and diffraction grating 6 until part of it arrives at exit 7.

FIG. 2 illustrates the above arrangement producing stray light. As shown, light reflected twice by diffraction grating 6 and thrice by concave mirror 5 comes out as stray light 9. Stray light 9 is light of wavelengths other than desired lengths. It must be eliminated because, if allowed to reach exit 7, it can lead to an error in spectroscopic analysis.

FIG. 3 shows the spectrum of outgoing light 8 of FIG. 2. In FIG. 3 the primary light is the optical output required, and the secondary light represents higher harmonics of the primary light. The spectrum shows stray light emerging between the primary light and secondary light. The point where stray light appears shifts as diffraction grating 6 turns.

In order to eliminate stray light 9, as is obvious from FIG. 2, it is only necessary to reduce the frequency of light reflection between concave mirror 5 and diffraction grating 6 lest any reflected light other than the primary light find its way to exit 7. Reduction of reflection frequency might simply be achieved by extending plane mirror 4, concave mirror 5, and diffraction grating 6 laterally, or horizontally, as viewed in FIG. 2. However, this would pose a problem of increased size of the Littrow spectroscope.

Stray light might also be excluded by connecting exit 7 with a filter that passes only the light of desired wavelengths. However, it would call for too many filters to be practicable, because the outgoing light that results from the rotation of diffraction grating 6 involves light output of a wide band.

OBJECT OF THE INVENTION

This invention is aimed at the elimination of the stray light inherent to the Littrow spectroscope.

DESCRIPTION OF THE PREFERRED EMBODIMENTS

Figure 4:
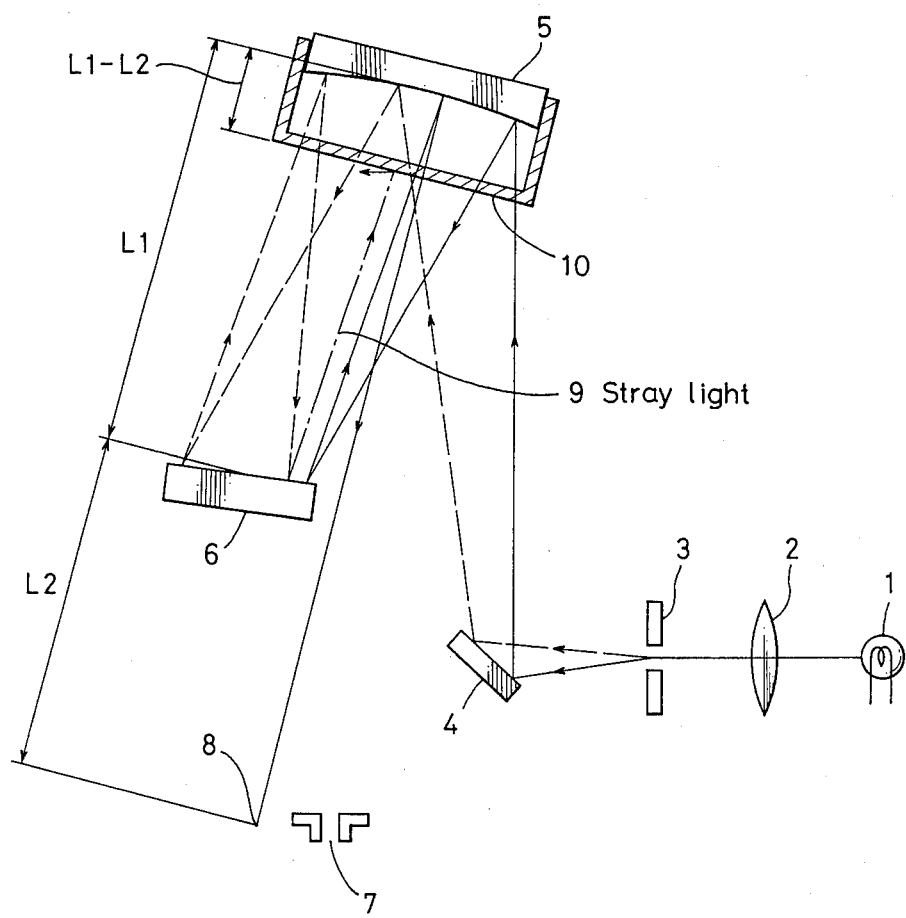
FIG. 4 is a schematic view of a Littrow spectroscope with a stray-light suppressor 10 embodying the invention.

Referring to the drawings, specifically to FIG. 4, there is illustrated the general construction of an embodiment of the invention.

Figure 1:
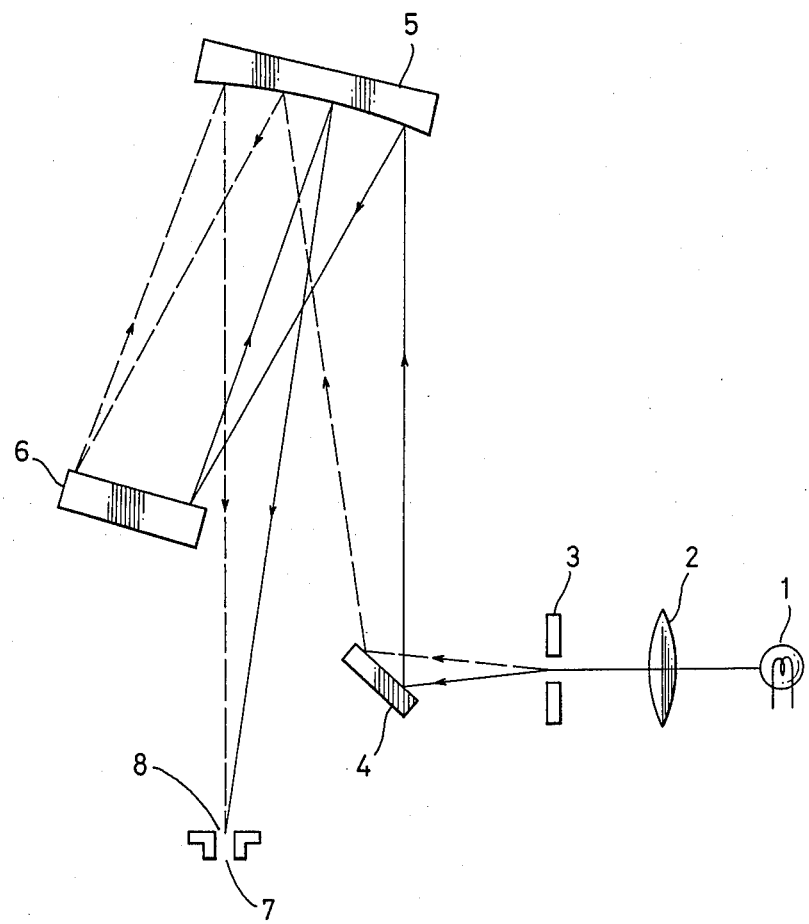
FIG. 1 is a schematic view of a conventional Littrow spectroscope.
Figure 2:
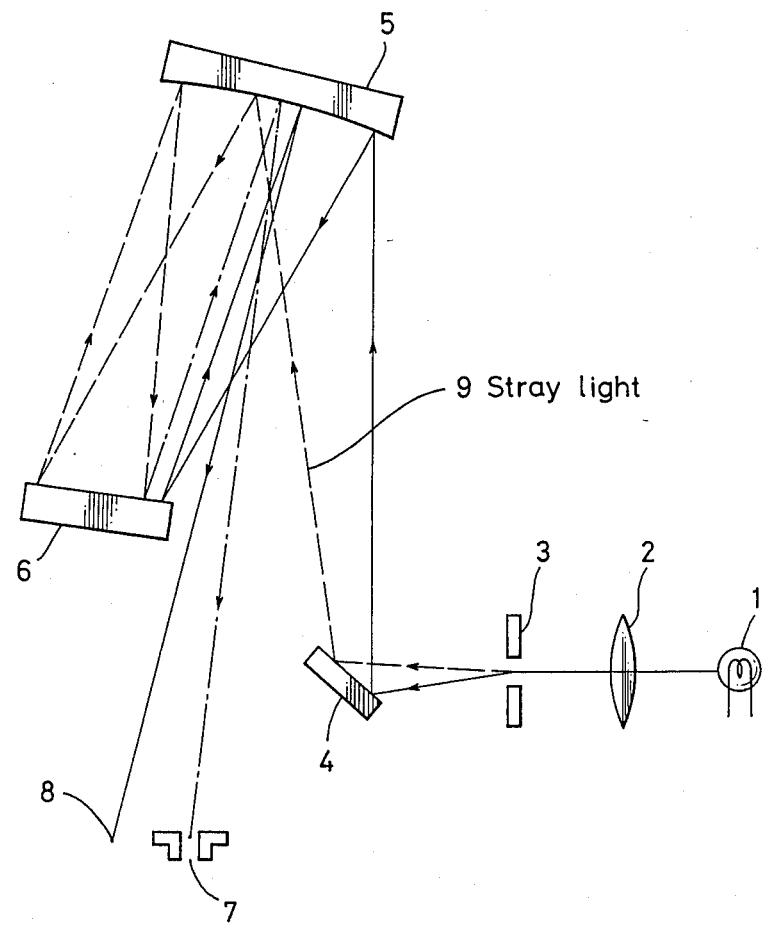
FIG. 2 is a view similar to FIG. 1 but showing stray light 9 being produced.

FIG. 4 shows the spectroscope of FIG. 1 which incorporates the stray-light suppressor 10 according to this invention, with stray light 9 incident of the suppressor. Stray light 9, reflected by stray-light suppressor 10 sideways, no longer falls upon exit 7.

Figure 5:
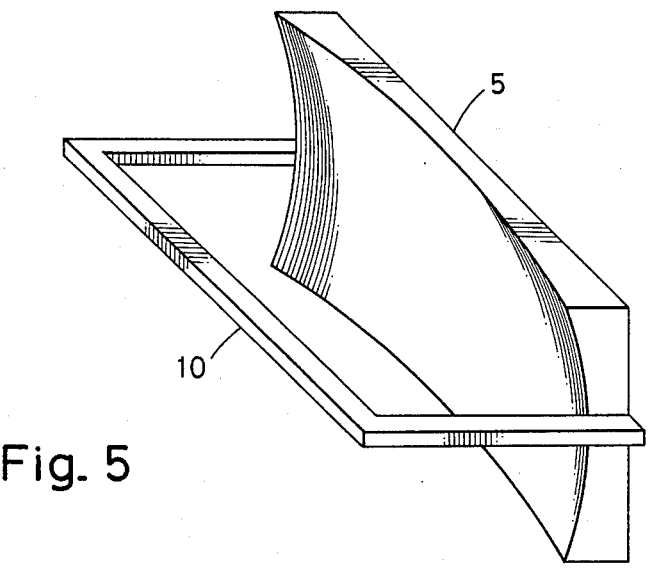
FIG. 5 is an outward view of stray-light suppressor 10.

Outward appearance of stray-light suppressor 10 is shown in FIG. 5. The suppressor takes the form of a narrow bar or strip held in front of concave mirror 5, horizontally in parallel with the longitudinal central axis of the mirror.

Stray-light suppressor 10 is installed in position chosen in the following manner. The distance between concave mirror 5 and diffraction grating 6 is assumed to be L1 and the distance between 6 and exit 7 to be L2, and then stray-light suppressor 10 is held a distance of (L1−L2) ahead of concave mirror 5. This allows stray light 9 to focus on stray-light suppressor 10.

Since light to be focused on exit 7 travels a distance (L1+L2) from concave mirror 5, the light reflected by diffraction grating 6 focuses at the point (L1−L2).

Figure 3:
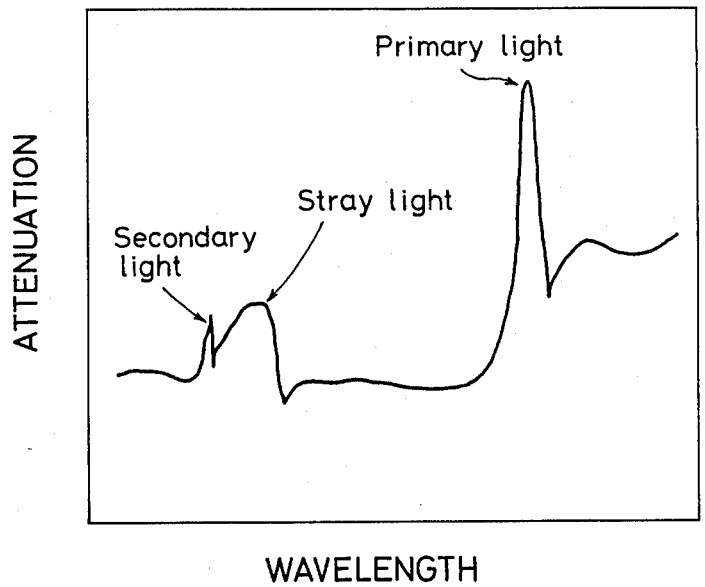
FIG. 3 is the spectrum of outgoing light in FIG. 2.
Figure 6:
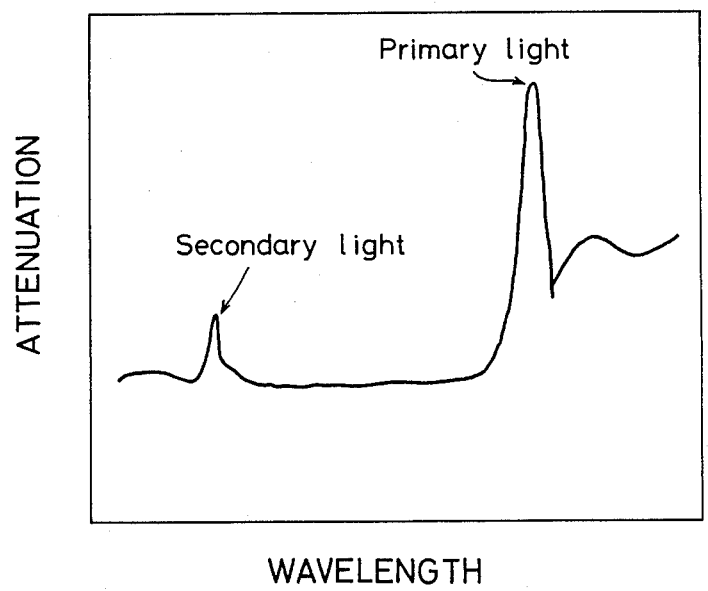
FIG. 6 is the spectrum of outgoing light in FIG. 4.

FIG. 6 carries the spectrum of outgoing light of FIG. 4. Only the primary light and secondary light of FIG. 3 are left behind; the stray light in FIG. 3 is non-existent here.

According to this invention, stray-light suppressor 10 of simple construction is disposed in front of concave mirror 5 and thereby stray light 9 inherent to the Littrow spectroscope can be eliminated.

Figure 7:
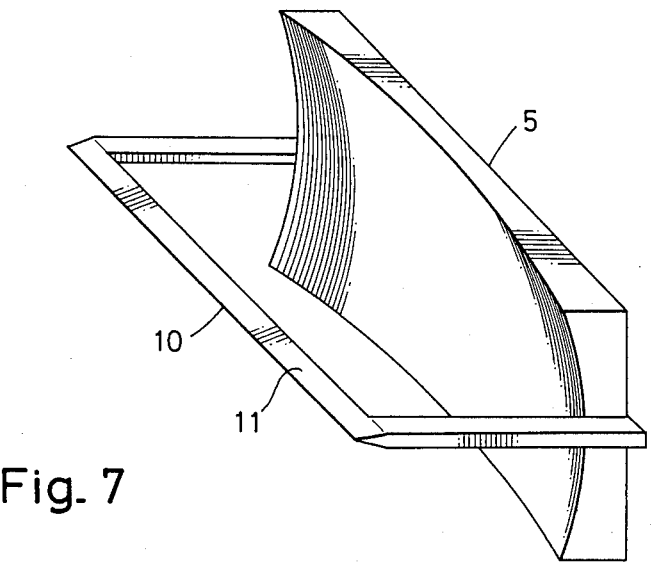
FIG. 7 is an outward view of another embodiment of the stray-light suppressor according to the invention.

Another embodiment of the invention will now be described. Outward appearance of a stray-light suppressor 10 which replaces the first embodiment is shown in FIG. 7.

Stray-light suppressor 10 in the form of a strip is held in front of, and horizontally in parallel with the longitudinal central axis of, concave mirror 5. The strip portion upon which stray light 9 impinges is tapered outwardly as viewed from the mirror. Stray light 9 incident upon the tapered edge 11 of stray-light suppressor 10 is reflected in directions other than those of diffraction grating 6 and exit 7. Hence, no stray light emission through exit 7.

According to the invention, stray-light suppressor 10 with the tapered edge, disposed in front of concave mirror 5, can eliminate stray light 9 inherent to Littrow spectroscope, directing it away from the path leading to the normal exit for the outgoing light.

What is claimed is:

1. For use with a Littrow spectroscope including a concave mirror for reflecting light from a source, a diffraction grating for further reflecting the light reflected by the concave mirror, said diffraction grating being made rotatable to allow said concave mirror to re-reflect the light therefrom, and an exit on which the light re-reflected by the mirror is focused; a stray-light suppressor in the form of a strip disposed in front of, and horizontally in parallel with the longitudinal. central axis of, said concve mirror, said suppressor being held in front of said concave mirror at a distance of (L1−L2) therefrom, where L1 is the distance between said concave mirror and said diffraction grating and L2 is the distance between said grating and said exit.

2. For use with a Littrow spectroscope including a concave mirror for reflecting light from a source, a diffraction grating for further reflecting the light reflected by the concave mirror, said diffraction grating being made rotatable to allow said concave mirror to re-reflect the light therefrom, and an exit on which the light re-reflected by the mirror is focused; a stray-light suppressor in the form of a strip disposed in front of, and horizontally in parallel with the longitudinal central axis of, said concave mirror, said suppressor being tapered in the portion upon hich the stray light from said diffraction grating impinges.

* * * * *